United States Patent
Pohl et al.

(10) Patent No.: US 7,771,665 B2
(45) Date of Patent: Aug. 10, 2010

(54) CHEMICAL DELIVERY ASSEMBLY

(75) Inventors: Jeffrey C. Pohl, Fort Wayne, IN (US); Angela M. Wiggs, North Webster, IN (US)

(73) Assignee: Group Dekko, Inc, Kendallville, IN (US)

( * ) Notice: Subject to any disclaimer, the term of this patent is extended or adjusted under 35 U.S.C. 154(b) by 0 days.

(21) Appl. No.: 12/013,736

(22) Filed: Jan. 14, 2008

(65) Prior Publication Data
US 2008/0169355 A1    Jul. 17, 2008

Related U.S. Application Data

(60) Provisional application No. 60/884,683, filed on Jan. 12, 2007.

(51) Int. Cl.
*A61L 9/03* (2006.01)
(52) U.S. Cl. .................................... 422/125; 422/300
(58) Field of Classification Search ................... None
See application file for complete search history.

(56) References Cited

U.S. PATENT DOCUMENTS

| | | | |
|---|---|---|---|
| 1,609,958 A | 12/1926 | Perrault | |
| 3,976,049 A | 8/1976 | Yamashita et al. | 126/263 |
| 4,163,038 A * | 7/1979 | Nishimura et al. | 422/36 |
| 4,171,340 A * | 10/1979 | Nishimura et al. | 422/36 |
| 4,228,124 A * | 10/1980 | Kashihara et al. | 422/36 |
| 5,429,271 A | 7/1995 | Porter | |
| 6,309,598 B1 | 10/2001 | Tully | 422/28 |
| 6,435,423 B2 | 8/2002 | Hurry et al. | 239/34 |
| 7,081,211 B2 | 7/2006 | Li et al. | 252/70 |
| 7,235,187 B2 | 6/2007 | Li et al. | 252/70 |
| 2002/0141898 A1 | 10/2002 | Carlucci et al. | 422/5 |
| 2002/0174863 A1 | 11/2002 | Saric et al. | 126/263.05 |
| 2006/0039685 A1 | 2/2006 | Berrido et al. | 392/392 |
| 2007/0148293 A1 | 6/2007 | Lindsay et al. | 426/112 |
| 2007/0237498 A1 | 10/2007 | Helf et al. | |

* cited by examiner

*Primary Examiner*—Elizabeth L McKane
(74) *Attorney, Agent, or Firm*—Taylor & Aust, P.C.

(57) ABSTRACT

A chemical delivery assembly includes a heating element which provides an exothermic chemical reaction, a chemical storage device configured for emitting a volatilized chemical therefrom, and a container including a bottom section and a top section, the heating element coupled with the bottom section, the chemical storage device coupled with the top section, the heating element being in thermal communication with the chemical storage device.

20 Claims, 4 Drawing Sheets

CHEMICAL DELIVERY ASSEMBLY

CROSS REFERENCE TO RELATED APPLICATIONS

This is a non-provisional application based upon U.S. provisional patent application Ser. No. 60/884,683, entitled "SINGLE USE DISPOSABLE CHEMICAL VAPORIZING DEVICE", filed Jan. 12, 2007, which is incorporated herein by reference.

BACKGROUND OF THE INVENTION

1. Field of the Invention

The present invention relates to chemical delivery assemblies, and, more particularly, to chemical vaporizing assemblies.

2. Description of the Related Art

An aroma delivery device is known which is used in conjunction with a consumable product. A problem with such an aroma delivery device is that it is not a stand-alone device. Further, an air treatment apparatus is known which employs a refill pack containing wax or paraffin granules incorporating a fragrance. A problem with such an air treatment apparatus is that it is not designed as a single-use, disposable apparatus.

What is needed in the art is an inexpensive, single-use, disposable, stand-alone chemical delivery assembly which uses an exothermic chemical reaction to heat a chemical storage device of the chemical delivery assembly.

SUMMARY OF THE INVENTION

The present invention provides an inexpensive, single-use, disposable, stand-alone chemical delivery assembly which uses an exothermic chemical reaction to heat a chemical storage device of the chemical delivery assembly.

The invention in one form is directed to a chemical delivery assembly including a heating element which provides an exothermic chemical reaction, a chemical storage device configured for emitting a volatilized chemical therefrom, and a container including a bottom section and a top section, the heating element coupled with the bottom section, the chemical storage device coupled with the top section, the heating element being in thermal communication with the chemical storage device.

The invention in another form is directed to a method of using a chemical delivery assembly, the method including the steps of providing, coupling, heating, communicating, and emitting. The providing step provides a heating element which provides an exothermic chemical reaction, a chemical storage device, and a container including a bottom section and a top section. The coupling step couples the heating element with the bottom section and the chemical storage device with the top section. The heating step heats the heating element. The communicating step thermally communicates the heating element with the chemical storage device. The emitting step emits a volatilized chemical from the chemical storage device.

An advantage of the present invention is that it is inexpensive.

Another advantage is that it can be a single-use, disposable chemical delivery assembly.

Yet another advantage is that it functions as a stand-alone assembly.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate one embodiment of the invention, and such exemplifications are not to be construed as limiting the scope of the invention in any manner.

DETAILED DESCRIPTION OF THE INVENTION

Figure 1:
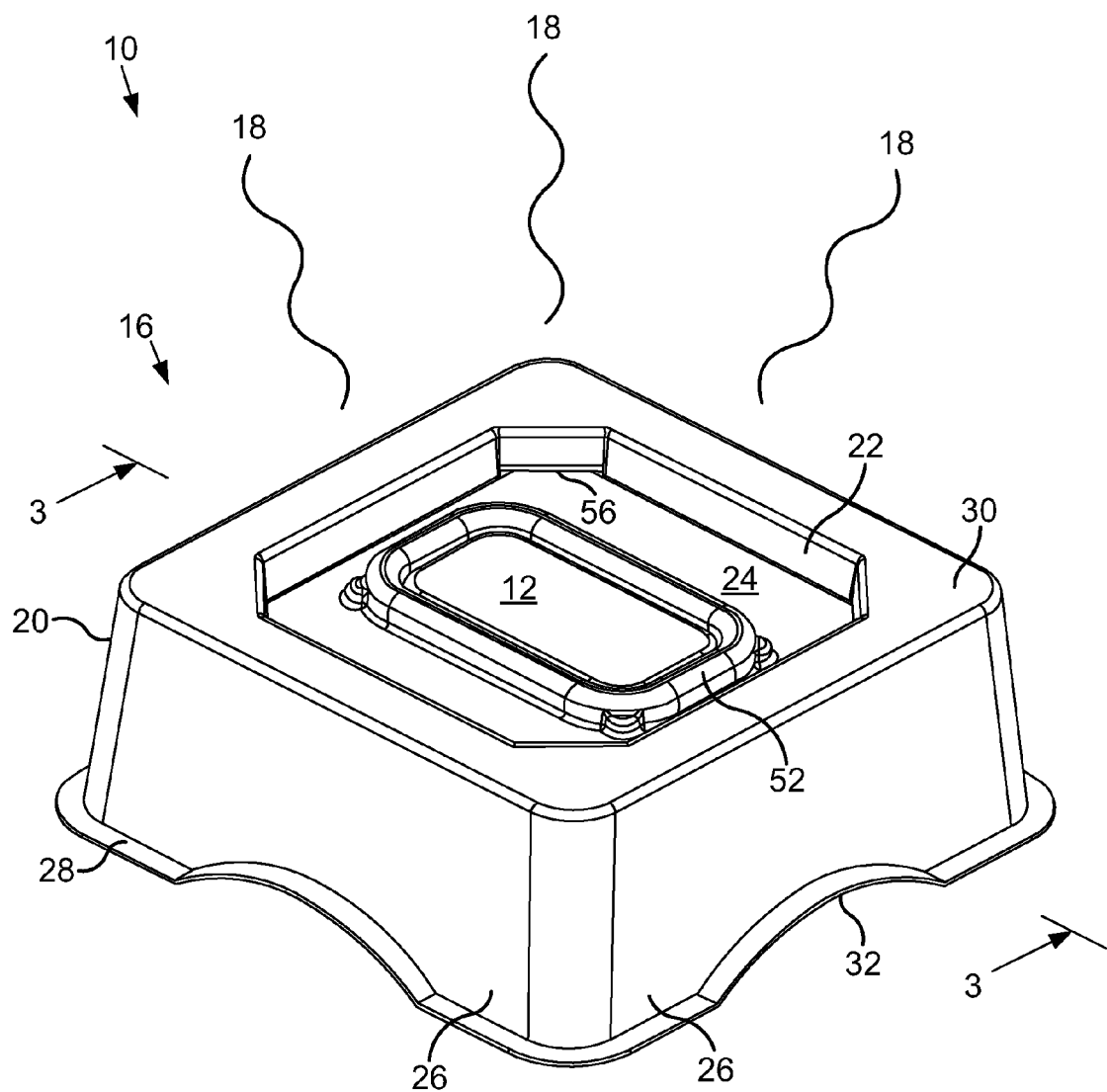
FIG. 1 is a top, perspective view of the chemical delivery assembly according to the present invention.
Figure 2:
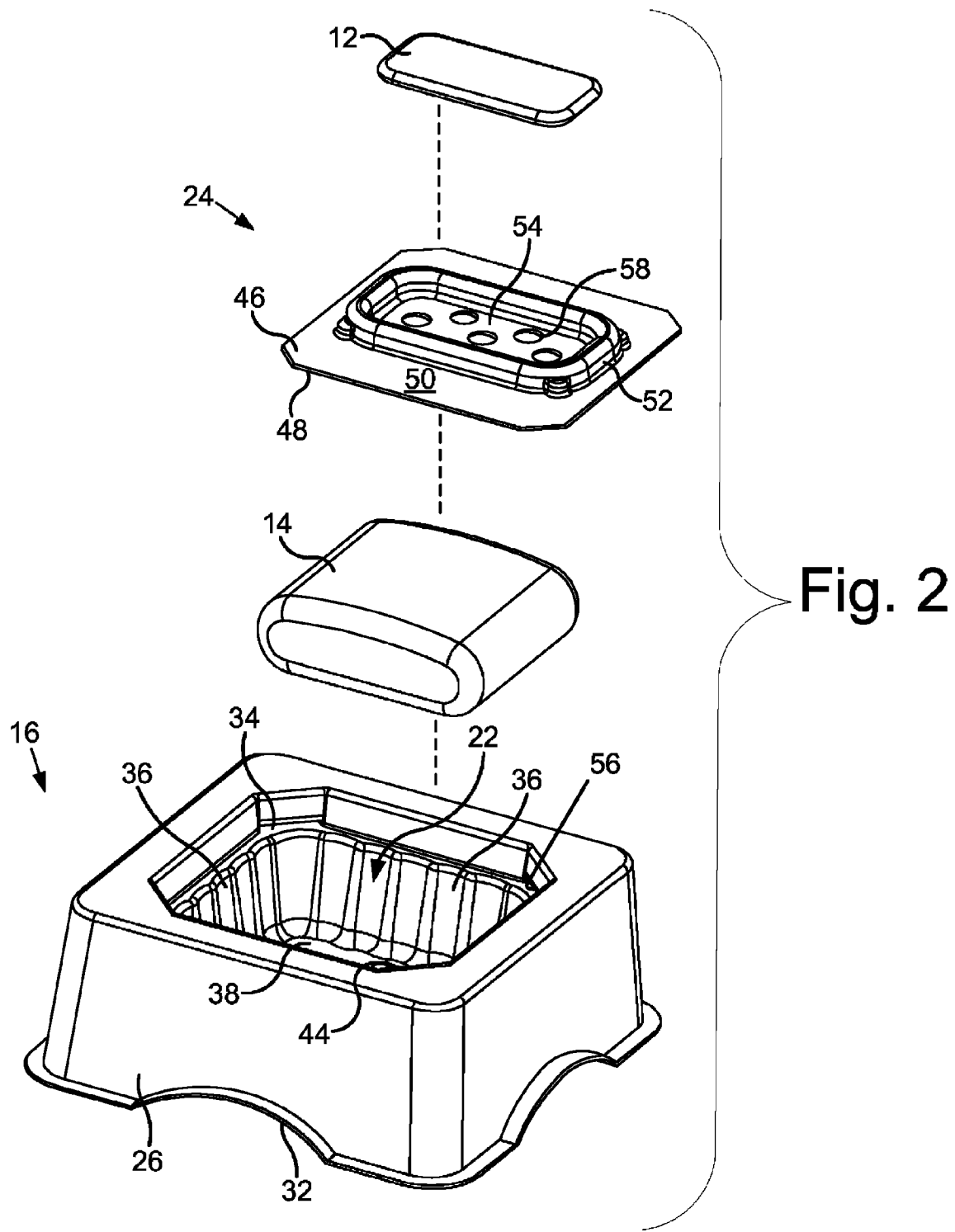
FIG. 2 is an exploded, perspective view of the chemical delivery assembly of FIG. 1.

Referring now to the drawings, and more particularly to FIGS. 1-2, there is shown a chemically delivery assembly 10 which generally includes a chemical storage device 12, a heating element 14, and a container 16. Chemical delivery assembly 10 can be an air freshener/deodorizer assembly, an air cleaner assembly, a bug repellant assembly, an insecticide delivery assembly, and/or generally a vaporizer, for instance, for providing medicinal vapors to the surrounding air. This listing of applications of chemical delivery assembly 10 is not intended to be limiting.

Chemical storage device 12, when heated, emits a volatilized chemical 18. That is, chemical storage device 12, before being heated, includes a chemical that is volatilizable (or, stated another way, can become volatilized). Upon being heated, the chemical volatilizes and is emitted into the surrounding air as volatilized chemical 18. By volatilize, Applicants mean that the chemical can become volatile, can pass off as a vapor. Chemical storage device 12 can include a porous cotton material, for example, which is soaked with a liquid containing volatilizable chemical. Alternatively, chemical storage device can be formed of a plastic fiber material, for example, which holds a liquid, or a gel, containing the volatilizable chemical. Chemical storage device 12 is filled with any suitable air treating material, such as an air deodorizer, an insect repellent, an insecticide, a health care agent, or the like.

Heating element 14 provides an exothermic chemical reaction. This exothermic chemical reaction can be provided in at least one of two ways. The first way provides that heating element 14 is an air-activated oxidation reaction heater. In this instance, heating element 14 can be, for example, an iron oxide heater that, when exposed to air, experiences a chemical reaction which produces heat. That is, heating element 14 undergoes an exothermic chemical reaction and thereby produces heat when heating element 14 is exposed to oxygen from air, the oxygen reacting with one or more chemical constituents of heating element 14. The second way provides that heating element 14 is activated by some other way than simply exposing heating element 14 to air. This could include heating element 14 having chemical constituents that can be caused to react together when, for instance, an end-user bursts a container containing one of these constituents to cause these constituents to come together and react exothermically, or otherwise causes these chemical constituents to come together so as to chemically react. The chemical constituent in the container that bursts can be in the form of water, for example.

Figure 3:
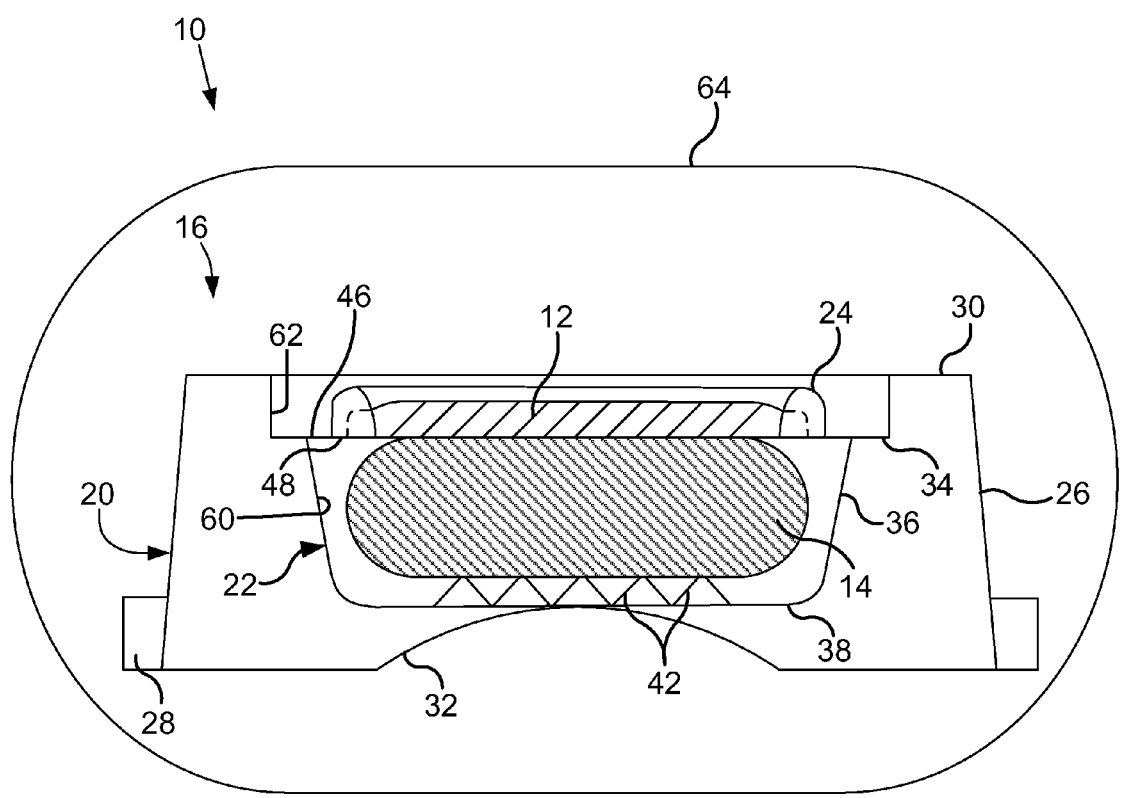
FIG. 3 is a schematic, sectional view of the chemical delivery assembly of FIG. 1 taken along line 3-3.

Container 16 includes a bottom section 60 and a top section 62 (sections 60 and 62 being shown in FIG. 3). Heating element 14 is coupled with bottom section 60, and chemical storage device 12 is coupled with top section 62. Container 16 can be an outer tray 16. Tray 16 includes a body 20, a dividing element 22, and a dividing element 24. Body 20 can be generally square-shaped and include four generally vertical side walls 26 (which can generally slant outwardly running from top to bottom), flanges 28 attached to the bottom of vertical walls 26 (flanges 28 providing a base for tray 16 to contact the surface on which tray 16 rests), and a top wall 30 which is generally parallel to base flanges 28 and to the flat surface (not shown) upon which chemical delivery assembly 10 rests. Side walls 26 serve as legs which support chemical delivery assembly 10 on the surface (not shown) as a stand-alone unit. Further, each of side walls 26 and the corresponding flanges 28 can define an arch 32 (or some differently shaped opening) so as to permit air surrounding the outer portion of tray 16 to easily flow under body 20 and to heating element 14. Body 20 is shaped so that chemical delivery assembly 10 can function as a stand-alone assembly/unit. That is, as a stand-alone assembly/unit, chemical delivery assembly 10 is not connected to another device to perform its function of delivering a volatilized chemical 18 into the surrounding air. Body 20 can be thermoformed plastic (i.e., using pneumatic and/or mechanical pressure forming, or vacuum forming).

Figure 4:
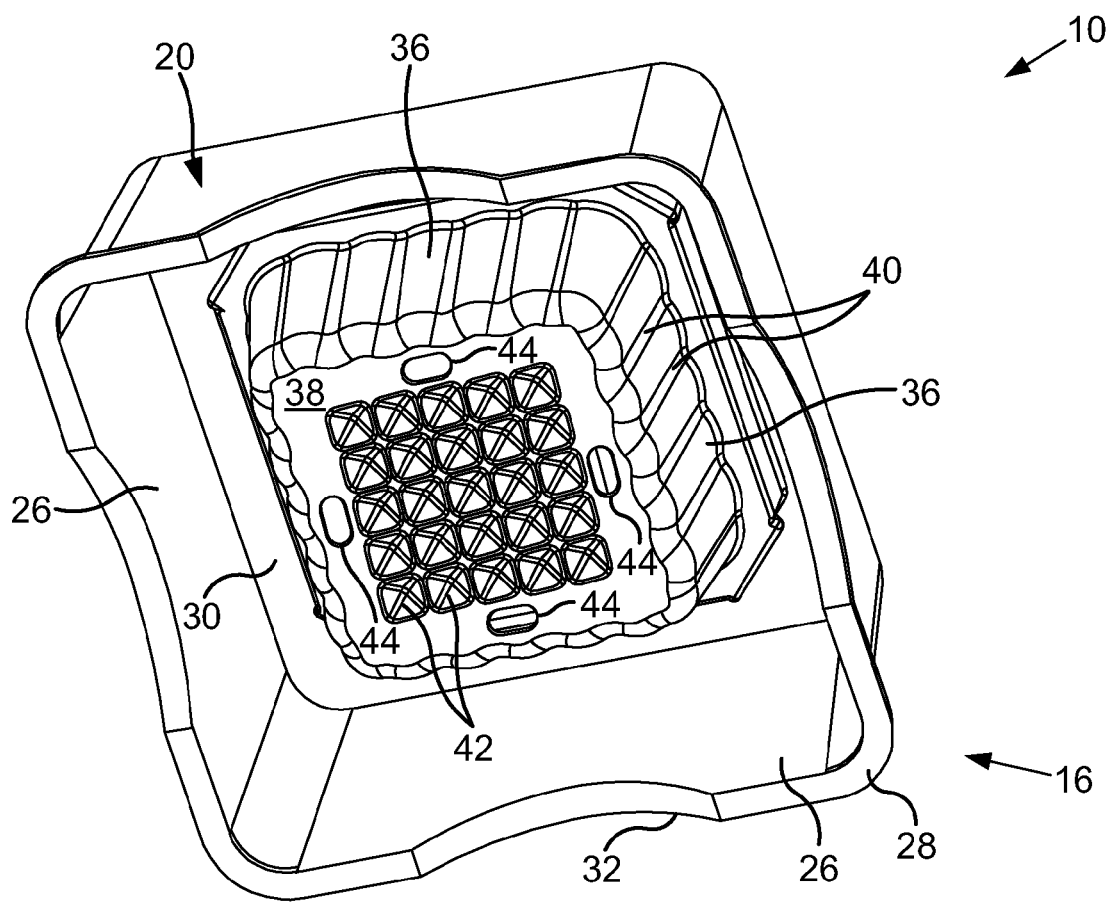
FIG. 4 is a bottom, perspective view of the chemical delivery assembly of FIG. 1.

Dividing element 22 forms a well which has an open surface along top wall 30 of body 20. Dividing element 22 can be made of the same material as body 20, formed at the same time as body 20, and be monolithic with body 20 (dividing element 22 being monolithic with body 20 is shown in the drawings). Dividing element 22 can include four generally vertical side walls 36 depending downwardly from top wall 30 of body 20 (these side walls 36 can decline inwardly running from top to bottom) and a bottom wall 38 connected to the lowest extent of side walls 36. Side walls 36 of dividing element 22 can include ribs 40 which help body 20 from crumbling when body 20 of tray 16 gets hot due to heating element 14. Bottom wall 38 can be formed so as to be positioned above the surface on which chemical delivery assembly 10 is situated given that legs 26 can be longer than side walls 36 of well 24. Bottom wall 38 serves as a mounting platform on which heating element 14 can rest or otherwise be affixed. Bottom wall 38 can include a plurality of raised projections 42 and a plurality of through-holes 44, as shown in FIGS. 3-4. Projections 42 serve to position heating element 14 above the lowest extent of bottom wall 38 such that heating element 14 does not sit flush on the lowest extent of bottom wall 38. Holes 44 permit air to be provided to heating element 14, the air flowing from the space separating side walls 26 and side walls 36 and from outside chemical delivery assembly 10 into that space via arches 32. By raising heating element 14 with projections 42, air is permitted to flow beneath heating element 14 and thereby to come into more surface area contact with the bottom surface of heating element 14 than if heating element 14 sat flush on bottom wall 38 formed as a flat expanse. When air is provided through holes 44 to heating element 14, heating element 14 heats up and thereby heats chemical storage device 12 so that chemical storage device 12 emits volatilized chemical 18.

Dividing element 24 includes two opposing sides 46 and 48. Heating element 14 is mounted on tray 16 to side 46, and chemical storage device 12 is mounted on tray 16 to side 48. In mounting to side 46, heating element 14 may or may not contact side 46. In the embodiment shown in the drawings, chemical storage device 12 is mounted on dividing element 24. Heating element 14 is in thermal communication with chemical storage device 12 via dividing element 24.

Dividing element 24 can be formed as a second tray (i.e., an inner tray 24) which snap-fittingly engages dividing element 22. Dividing element 24 includes a platform 50 (i.e., a wall 50) and a ridge 52 which can be monolithically formed with platform 50. Dividing element 24 forms a tray such that dividing element 24 defines its own well 54 formed by platform 50 and ridge 52. Platform 50 has a generally flat expanse and four corners, although the corners do not necessarily form pointed tips. When dividing element 24 is assembled with outer tray 16, the corners of platform 50 can snap-fit into corresponding slots 56 formed in dividing element 22. Further, these corners, as well as the longitudinal and transverse edges, of platform 50 can rest on a generally horizontal shoulder 34 formed on dividing element 22. Platform 50 can define a plurality of through-holes 58 for directing heat from heating element 14 into chemical storage device 12. Ridge 52 can form an upstanding wall on platform 50, ridge 52 connecting to itself so as to encircle a portion of platform 50; such encircling is meant to include various shapes, such as a circle, an ellipse, a rectangle, and the like. Ridge 52 serves to secure chemical storage device 12 when chemical storage device 12 is mounted on platform 50. Together, the solid portion of platform 50 within well 54 of dividing element 24 and through-holes 58 provide a heat transfer plate which permits the appropriate heat transfer rate from heating element 14 to chemical storage device 12. That is, the solid portion of platform 50 beneath chemical storage device 12 provides for a predetermined rate of heat transfer via conduction, and through-holes 58 beneath chemical storage device 12 provide for a predetermined rate of heat transfer via convection. Rather than having a plurality of through-holes 58, dividing element 24 may have a single hole 58 sized to provide an optimal heat transfer rate from heating element 14 to chemical storage device 12. Dividing element 24 can prevent heating element 14 from being in direct contact with chemical storage device 12, as shown in the drawings. Dividing element 24 can alternatively have a clam-shell design (not shown); that is, dividing element 24 can also include a lid which lies over chemical storage device 12, the lid being similar in appearance to dividing element 24 as shown in the drawings but turned upside down.

Dividing element 24 divides bottom section 60 from top section 62 of container 16. More specifically, side 48 (the bottom side in the drawings) of dividing element 24 divides bottom section 60 from top section 62. Alternatively, one can view shoulder 34 as the dividing line between bottom section 60 and top section 62.

Dividing element 24 can be thermoformed separately from body 20 of tray 16, as chemical storage device 12 and heating element 14 can be formed separately from body 20 of tray 16. Dividing element 24, body 20 and well 22 of tray 16, chemical storage device 12, and heating element 14 can then be assembled with ease in their respective positions during manufacturing to form a single chemical delivery assembly 10. During assembly of chemical delivery assembly 10, heating element 14 can first be placed on projections 42 of bottom wall 38 of well 22. Then, dividing wall 24 can be snap-fittingly engaged with well 22. Then, chemical storage device 12 can be set on, or otherwise mounted to, dividing wall 24. Then, once these parts 12, 14, 16 (which includes dividing elements 22 and 24) are assembled together to form chemical delivery assembly 10, a container 64 can be used to enclose these parts 12, 14, 16 as an assembled group. The container 64 can be used to enclose a vacuum inside such that heating element 14 is in a vacuum and thus not in contact with air before chemical delivery assembly 10 is ready to be used by an end-user. Alternatively, the container 64 can be such that it does not enclose a vacuum therein. In this alternative, a very small amount of air may be enclosed/sealed in the container 64 (so as to avoid having to vacuum seal the container), but this small amount is effectively a negligible amount in the sense that heating element 14 either does not yet begin to heat up or any heating that does occur is very minimal and does not manage to use up heating element 14 before an end-user has the chance to open the container 64 and to use effectively chemical delivery assembly 10. The container 64 is heat-sealed closed so as to enclose chemical delivery assembly 10. The container 64 can be made of a biaxially-oriented polyethylene terephthalate polyester ("boPET") film and can be, for example, MYLAR. The boPET film can be aluminized, which can render the container 64 even less permeable to gasses. As such, the metallized boPET film (which can be referred to as a "foil") can protect the contents of the container 64 against oxidation. Alternatively, dividing element 24 can be formed monolithically with body 20 of tray 16.

Chemical delivery assembly 10 can be a single-use, disposable assembly. That is, chemical delivery assembly 10 is manufactured inexpensively and designed to be discarded when it no longer emits volatilized chemical 18. Chemical delivery assembly 10 no longer emits volatilized chemical 18 when heating element 14 ceases to produce heat and/or chemical storage device 12 no longer contains the volatilizable chemical. Further, chemical delivery assembly 10 can have a relatively short life span. That is, chemical delivery assembly 10 may cease to function (as described above) after about forty-eight hours. Chemical delivery assembly 10 may not be designed such that an end-user can replace heating element 14 and/or replace or refill chemical storage device 12.

In use, chemical delivery assembly 10 is removed from the container 64 and placed on a surface (i.e., a floor of a room). Upon doing so, an abundance of air is provided to heating element 14 via holes 44. Upon being provided with a sufficient amount of air, heating element 14 produces an exothermic chemical reaction which eventually heats chemical storage device 12. Upon being heated (or at least to a certain, predetermined degree), chemical storage device 12 emits volatilized chemical 18 into the air surrounding chemical delivery assembly 10. When heating element 14 stops producing heat or when chemical storage device 12 has exhausted its supply of the volatilizable chemical, chemical delivery assembly 10 is discarded. Alternatively, if chemical delivery assembly is designed such that heating element 14 is activated using another way besides air-activation (as described above), chemical delivery assembly 10 can be designed so that heating element 14 is accessible to an end-user in order to activate heating element 14 or is accessible using water, for example.

The present invention also provides a method of using chemical delivery assembly 10. The method includes the steps of providing, coupling, heating, communicating, and emitting. The providing step provides heating element 14 which provides an exothermic chemical reaction, chemical storage device 12, and container 16 including bottom section 60 and top section 62. The coupling step couples heating element 14 with bottom section 60 and chemical storage device 12 with top section 62. The heating step heats heating element 14. The communicating step thermally communicates heating element 14 with chemical storage device 12. The emitting step emits volatilized chemical 18 from chemical storage device 12. Chemical delivery assembly can be a single-use, disposable assembly. Container 16 can be a first tray 16 which includes dividing element 24 which divides top section 62 from bottom section 60, chemical storage device 12 being mounted on dividing element 24, heating element 14 being in thermal communication with chemical storage device 12 via said dividing element 24. Tray 16 can include dividing element 22, dividing element 24 including a second tray 24 and being snap-fittingly engaged with dividing element 22. The method can further include directing heat into chemical storage device 12 using holes 58 defined by wall 50 of tray 24. The method can further include mounting heating element 14 to dividing element 22 of said tray 16 and providing air to heating element 14 using holes 44 defined by dividing element 22. When air is provided to heating element 14, heating element 14 heats up and thereby heats chemical storage device 12 so that chemical storage device 12 emits volatilized chemical 18. Tray 16 includes body 20 which supports chemical delivery assembly 10 as a stand-alone unit, body 20 being monolithic with dividing element 22.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A chemical delivery assembly, comprising:
   an air-activated heating element which provides an exothermic chemical reaction;
   a chemical storage device configured for emitting a volatilized chemical therefrom;
   a container including a bottom section and a top section, said heating element coupled with said bottom section, said chemical storage device coupled with said top section, said heating element being in thermal communication with said chemical storage device, said container further including a dividing element which divides said bottom section from said top section, said chemical storage device being mounted on said dividing element, said heating element being in thermal communication with said chemical storage device via said dividing element, said dividing element including a flat platform and an upstanding wall connected to said platform and spaced radially inwardly relative to an outer perimeter of said platform, said upstanding wall encircling said chemical storage device, said container further including a top edge and an inwardly extending horizontal shoulder spaced downwardly from said top edge, said platform of said dividing element resting on and directly contacting said shoulder.

2. The chemical delivery assembly of claim 1, wherein said chemical delivery assembly is a single-use, disposable assembly.

3. The chemical delivery assembly of claim 1, wherein said container is a first tray which includes said dividing element which is a first dividing element.

4. The chemical delivery assembly of claim 3, wherein said first tray includes a second dividing element, said first dividing element including a second tray and being snap-fittingly engaged with said second dividing element.

5. The chemical delivery assembly of claim 4, wherein said second tray includes a wall with a first plurality of holes formed therein, said first plurality of holes configured for directing heat into said chemical storage device.

6. The chemical delivery assembly of claim 4, wherein said container includes a plurality of exterior side walls and a top wall, said plurality of exterior side walls configured for supporting the chemical delivery assembly on a surface, said top wall connecting said second dividing element with said plurality of exterior side walls, said second dividing element depending from said top wall, being spaced apart from said plurality of exterior side walls, and supporting said first dividing element.

7. The chemical delivery assembly of claim 3, wherein said first tray includes a second dividing element, said heating element mounted to said second dividing element, said second dividing element including a plurality of holes configured for permitting air to be provided to said heating element.

8. The chemical delivery assembly of claim 7, wherein, when air is provided to said heating element, said heating element is configured for heating up and thereby heating said chemical storage device so that said chemical storage device emits said volatilized chemical.

9. The chemical delivery assembly of claim 7, wherein said first tray includes a body configured for supporting the chemical delivery assembly as a stand-alone unit, said body being monolithic with said second dividing element.

10. A method of using a chemical delivery assembly, said method comprising the steps of:
providing an air-activated heating element which provides an exothermic chemical reaction, a chemical storage device, and a container including a bottom section and a top section;
coupling said heating element with said bottom section and said chemical storage device with said top section;
heating said heating element;
thermally communicating said heating element with said chemical storage device, said container further including a dividing element which divides said bottom section from said top section, said chemical storage device being mounted on said dividing element, said heating element being in thermal communication with said chemical storage device via said dividing element, said dividing element including a flat platform and an upstanding wall connected to said platform and spaced radially inwardly relative to an outer perimeter of said platform, said upstanding wall encircling said chemical storage device, said container further including a top edge and an inwardly extending horizontal shoulder spaced downwardly from said top edge, said platform of said dividing element resting on and directly contacting said shoulder; and
emitting a volatilized chemical from said chemical storage device.

11. The method of claim 10, wherein the chemical delivery assembly is a single-use, disposable assembly.

12. The method of claim 10, wherein said container is a first tray which includes said dividing element which is a first dividing element.

13. The method of claim 12, wherein said first tray includes a second dividing element, said first dividing element including a second tray and being snap-fittingly engaged with said second dividing element.

14. The method of claim 13, further including the step of directing heat into said chemical storage device using a first plurality of holes defined by a wall of said second tray.

15. The method of claim 13, wherein said container includes a plurality of exterior side walls and a top wall, said plurality of exterior side walls configured for supporting the chemical delivery assembly on a surface, said top wall connecting said second dividing element with said plurality of exterior side walls, said second dividing element depending from said top wall, being spaced apart from said plurality of exterior side walls, and supporting said first dividing element.

16. The method of claim 12, further including the steps of mounting said heating element to a second dividing element of said first tray and providing air to said heating element using a plurality of holes defined by said second dividing element.

17. The method of claim 16, wherein, when air is provided to said heating element, said heating element heats up and thereby heats said chemical storage device so that said chemical storage device emits said volatilized chemical.

18. The method of claim 16, wherein said first tray includes a body which supports the chemical delivery assembly as a stand-alone unit, said body being monolithic with said second dividing element.

19. A chemical delivery assembly, comprising:
an air-activated heating element which provides an exothermic chemical reaction;
a chemical storage device configured for emitting a volatilized chemical therefrom;
a container including a top edge and an inwardly extending horizontal shoulder spaced downwardly from said top edge, said air-activated heating element and said chemical being located within said container in thermal communication with each other;
a dividing element, said chemical storage device being mounted on said dividing element, said heating element being in thermal communication with said chemical storage device via said dividing element, said dividing element including a flat platform and an upstanding wall connected to said platform and spaced radially inwardly relative to an outer perimeter of said platform, said upstanding wall encircling said chemical storage device, said platform of said dividing element resting on and directly contacting said shoulder; and
a removable sealing device configured for sealing said air-activated heating element and said chemical storage device from ambient air.

20. The chemical delivery assembly of claim 19, wherein said sealing device is a closure adhered to said container.

* * * * *